United States Patent [19]

McCreery et al.

[11] 4,395,312

[45] Jul. 26, 1983

[54] METHOD AND APPARATUS FOR THE ANALYSIS OF SOLUTION ADJACENT AN ELECTRODE

[75] Inventors: Richard L. McCreery; Clyde W. McCurdy; Paula J. Rossi, all of Columbus, Ohio

[73] Assignee: The Ohio State University Research Foundation, Columbus, Ohio

[21] Appl. No.: 250,168

[22] Filed: Apr. 2, 1981

[51] Int. Cl.³ .......................................... G01N 27/46
[52] U.S. Cl. .................... 204/1 T; 204/400; 356/300; 356/319; 436/805; 436/806
[58] Field of Search .......................... 204/1 T, 195 R; 356/300, 305, 309, 317, 318, 319, 323, 326, 328, 432; 436/805, 806

[56] References Cited

U.S. PATENT DOCUMENTS

| | | | |
|---|---|---|---|
| 3,708,402 | 1/1973 | Bean | 204/299 |
| 3,947,124 | 3/1976 | West | 356/74 |
| 4,217,195 | 8/1980 | Uzgiris et al. | 204/180 R |
| 4,252,617 | 2/1981 | Heusler et al. | 204/195 R |
| 4,274,937 | 6/1981 | Findl et al. | 204/195 R |
| 4,306,877 | 12/1981 | Lubbers | 204/195 M |

OTHER PUBLICATIONS

Heineman, "Analytical Chemistry", vol. 50, (Mar. 1978), p. 390A.
Tyson et al., "Analytical Chemistry", vol. 26, (1979), pp. 117–125.
Tyson et al., "Analytical Chemistry", vol. 27, (1980), pp. 335–342.

Primary Examiner—T. Tung
Attorney, Agent, or Firm—Millard & Cox

[57] ABSTRACT

Electrochemically generated chromophores are measured by passing a beam of electromagnetic radiation parallel and close to the surface of the electrode at which they are being generated, and collecting the diffracted radiation. The response is so rapid (~0.025 sec.) that modulation is practicable and the path length, which is set by the thickness of the electrode, is much greater than in optically transparent electrodes, thus rendering the method very sensitive to weak chromophores or low concentrations.

25 Claims, 14 Drawing Figures

METHOD AND APPARATUS FOR THE ANALYSIS OF SOLUTION ADJACENT AN ELECTRODE

The government has rights in this invention pursuant to a grant #CHE 7828068 awarded by the National Science Foundation.

BACKGROUND OF THE INVENTION

The invention relates to a method for the analysis of a layer of solution adjacent a surface of an electrode.

Electrochemistry has for a long period been extensively used for the analysis of solutions, including analysis of the generation of reactive species in solution, usually on a time scale of a few tens of seconds down to the sub-millisecond range. Most electrochemical analysis is effected with controlled potential experiments, such as voltammetry and chronoamperometry, in which a controlled potential is applied to the electrode and the current passing through the electrode is monitored and used to deduce mechanistic and thermodynamic data as well as concentrations. While such methods dependent upon current measurement have yielded much useful analytical data, such methods often suffer from an inherent lack of selectivity. Voltammetry is a low-resolution method, making it difficult to measure a single trace component in the presence of other species. Faradaic reactions of adsorbed molecules or the electrode itself may generate significant "noise" signals, making it impossible to detect very small concentrations of solution components in many cases. In addition, double layer chrging current is always present in voltammetry, and this double-layer charging current also serves to lower the sensitivity to components present in only small amounts. Moreover, in voltammetric experiments, the observed current may be due to reactions of several different species in the solution and, if the chemical changes involved are complex, the mere observation of the overall current is often insufficient to enable one to deduce the mechanism of the chemical changes taking place, or even to measure an overall rate constant for the chemical change.

Thus, while voltammetric techniques are theoretically applicable to any componet of a solution which can undergo oxidation or reduction, the aforementioned problems severely limit the usefulness of the technique for analysis of complex organic mixtures such as biological fluids. The limitations of voltammetric techniques with biological fluids are still severe, despite the recent development of pulse techniques which allow analysis down to the $10^{-8}$ to $10^{-9}$ M concentration range in a few cases. Accordingly, although voltammetric techniques are used in certain instances, in most cases the aforementioned difficulties have prevented the application of voltammetric techniques to biological fluids without major sample preparation.

Recently so-called "spectroelectrochemical" methods have been developed which greatly increase the selectivity of electrochemical analytical methods. In spectroelectrochemical methods, electromagnetic radiation (usually either visible or ultraviolet) is passed through the layer of solution adjacent the electrode at which the electrochemical changes are taking place. The species present in this layer of solution will of course produce conventional absorption spectra, so that if a chromophore (a term which is used herein to mean a species which absorbs certain wave lengths of electromagnetic radiation, not necessarily in the visible spectrum) is generated or consumed in the electrochemical reactions taking place at the electrode, the progress of the reactions and the concentrations of the species involved may be determined by inspection of the absorption spectra produced. A variety of arrangements have been used for passing the beam of radiation through the layer of solution adjacent an electrode. Most of these arrangements involve the use of an optically transparent electrode either in the form of a transparent substance such as glass coated with a very thin, transparent layer of a conductive metal, or in the form of a metal grid having apertures therethrough. For example, a grid-type optically transparent electrode may be positioned in a thin layer (typically about 0.2 mm thick) of solution sandwiched between two transparent plates. A beam of light is then shone through this apparatus, which functions as a small transmission cell in exactly the same manner as the much thicker cells used in conventional spectrophotometers. Absorption spectra may be obtained from the metal-on-glass type of optically transparent electrode either by passing a beam of light through the electrode or by arranging for total internal reflection of light from the surface of the electrode. Finally, absorption spectra may be obtained by bouncing a beam of light off a polished electrode (which need not be of the optically transparent type).

It is also possible to generate a Raman spectrum of a layer of solution adjacent an electrode by bouncing an intense beam of light (usually from a laser) off the surface of an electrode and examining the Raman-scattered light.

A review of the aforementioned spectroelectrochemical techniques may be found in W. R. Heineman, Analytical Chemistry, 50, 390A (1978).

Unfortunately, all the techniques described above are very insensitive since the path length for absorbance by chromophores generated at the electrode is limited to the thickness of the electrochemical diffusion layer, which is typically about 0.1 mm. In the case of total internal reflection, the path length is even less since the internally reflected beam only penetrates on the order of a few micrometers into the solution layer. These very short path lengths render the techniques relatively insensitive; even when strong chromophores are being generated, the methods are not generally useful at chromophore concentrations below $10^{-5}$M, unless impractically long (about 100 second) electrolysis times are used. Moreover, because it is necessary to generate high concentrations of chromophores and establish a relatively thick diffusion layer of electrogenerated species in order to obtain sufficient absorbtion, spectroelectrochemical methods have not hitherto been generally usable when it is desired to study short-lived intermediates.

J. F. Tyson and T. S. West in Talanta 26, 117–125 (1979) and 27, 335–342 (1980) describe a spectroelectrochemical analytical method in which a light beam passes at grazing incidence over a platinum electrode. Electrogenerated chromophores in the solution layer adjacent the electrode selectivety absorb light from the beam and the beam is monitored after it has passed the electrode to determine the absorption occurring. Although this method is capable of improving the sensitivity of spectroelectrochemical measurements to some extent, it is difficult to control the grazing incidence of the beam sufficiently to obtain highly reproducible results and the method still demands the formation of a thick diffusion layer adjacent the electrode, so that electrolysis must be continued for a relatively long period, typically about 40 seconds. This renders the method useless for very short-lived species and prevents the method being used with modulation of the potential applied to the electrode. The use of such modulation is highly desirable because it can be used to improve greatly the sensitivity of the method.

There is thus a need for a spectroelectrochemical analytical method which does not require the formation of a thick diffusion layer and which thus permits the modulation of the voltage applied to the electrode in order to increase the sensitivity of the method. It is also desirable that such a method not be limited to an absorption path only equal to the thickness of the diffusion layer adjacent the electrode. This invention provides such a method.

SUMMARY OF THE INVENTION

The invention provides a method for the analysis of a layer of solution adjacent a surface of an electrode, said solution being capable of undergoing an electrochemical change which alters its absorbance of electromagnetic radiation of at least one wavelength, comprising passing a beam of electromagnetic radiation at least part of which is of said wavelength across and substantially parallel to the surface of the electrode, collecting at least part of the radiation *diffracted* at an angle to the original beam, altering the potential of the electrode, thereby causing at least part of the solution to undergo the electrochemical change, again passing the beam across and substantially parallel to the surface of the electrode, and again collecting at least part of the radiation diffracted at an angle to the original beam.

The electrochemical change which the solution undergoes in the instant method may involve the electrochemical generation of a chromophore (so that the absorbance of the solution is greater after the change than before) or may involve the electrochemical destruction of a chromophore (so that the absorbance of the solution is less after the change than before). Hereinafter, the invention will mainly be described with reference to the first of these two variants of the method, but it should be understood that, where hereinafter reference is made to the generation of a chromophore during electrolysis, the method may also be applied to the destruction of a chromophore during electrolysis.

Thus, unlike prior art methods which rely upon absorption of the original beam to produce data concerning any chromophores in the layer of solution adjacent the electrode, the instant method collects part or all of the diffracted light. Because diffraction only takes place very close to the electrode, the diffracted light effectively samples a very thin layer of solution near the electrode (typically a layer about 5 micrometers thick) so that the method does not require the formation of a thick diffusion layer to be effective. Thus, the method can be used to detect short-lived species and also allows modulation of the potential applied to the electrode, thus greatly improving the sensitivity of the method.

In the instant method, the beam of electromagnetic radiation is preferably monochromatic and is conveniently supplied by a laser. The radiation is preferably in the visible or ultraviolet part of the spectrum.

As already mentioned, the method allows for modulation of the potential applied to the electrode. Accordingly, in the instant method the potential at the electrode is preferably varied cyclicly and the variation of the intensity of the diffracted radiation with respect to time is determined and correlated with the variation of the potential at the electrode. In this case, conveniently the detector used to measure the diffracted radiation is coupled to a lock-in (a phase sensitive amplifier having a frequency dependent gain factor tuned to the frequency of the potential modulation). The modulation of the potential can be rapid and preferably has a frequency of at least about 10 Hz., and desirably at least about 50 Hz, but preferably not more than about 200 Hz.

As explained below, it is desirable to measure the intensity of the diffracted radiation at a plurality of angles with respect to the original beam since this yields data concerning the distribution of the electrogenerated species as it diffuses away from the electrode, information which is not readily obtainable by conventional spectroelectrochemical methods.

The electrode used in the instant method may have any form which permits a beam of radiation to pass parallel to the active electrode surface thereof. For example, the electrode might have the form of a flat plate with a circular aperture therethrough (so that the active electrode surface is the cylindrical surface of the aperture). This form of electrode has the advantage that, when the aperture is made much narrower than the beam, the electrode absorbs all the beam except the part passing through the aperture, thereby greatly reducing the amount of undiffracted light passing the electrode.

The beam of electromagnetic radiation may be passed over more than one surface of the electrode. In particular, for reasons discussed below, where it is desired to obtain information about the distribution of the chromophore relative to the distance from the electrode, it is advantageous to arrange for the beam to pass parallel to two parallel surfaces of the electrode. The necessary two parallel surfaces of the electrode may comprise two parallel surfaces forming opposed sides of a slot cut through the electrode. However, since the two parallel surfaces must be parallel with an accuracy comparable to that of the wavelength of the radiation used and since it is difficult to cut slots in metal electrodes with optical accuracy, it is preferred that the two parallel surfaces of the electrode comprise opposed faces of a laminar electrode, which is conveniently a metal foil. Obviously, it is much easier to secure metal foils whose thickness is constant with optical accuracy than to cut slots in solid metal electrodes with the necessary accuracy.

The instant method may be used for immunoassay by using as the solution a solution containing an antigen, part of which is bound to an antibody, the free and bound antigen differing in their electrochemical characteristics.

The invention also provides apparatus for analysis of a layer of solution adjacent a working electrode, this apparatus comprising the working electrode, a counterelectrode, means for applying a variable potential between the working and counterelectrodes, a beam generator for passing a beam of electromagnetic radiation across and substantially parallel to the surface of the working electrode, a container for retaining solution in contact with the surface of the working electrode and a radiation detector for detecting radiation diffracted at an angle to the beam. Desirably, a converging lens is disposed adjacent the working electrode on the opposed side thereof from the beam generator and the radiation detector is disposed in the focal plane of the lens. The radiation detector is conveniently a photomultiplier tube.

DETAILED DESCRIPTION OF THE DRAWINGS

Figure 1:
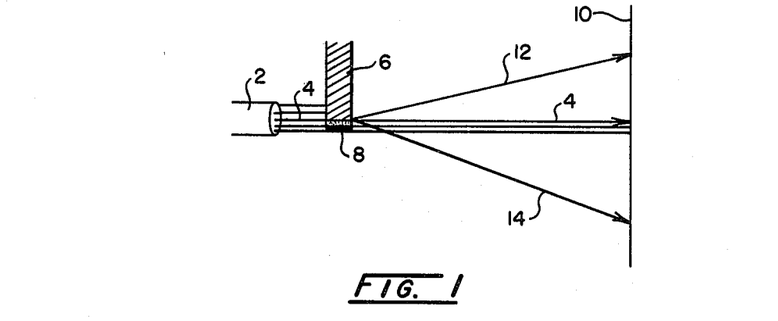
FIG. 1 shows schematically an apparatus for carrying out the instant method.

FIG. 1 shows an idealized apparatus of the invention. A laser 2 sends an intense beam 4 of monochromatic light towards a working electrode 6 of rectangular cross-section. Although not shown in the drawings, the working electrode 6 is electrically connected via a voltage regulator to a counterelectrode, the voltage regulator being able to vary the potential difference between the working and counterelectrodes. The counterelectrode is of course in contact with solution which is in fluid contact with that adjacent the working electrode 6. A diffusion layer 8 of electrogenerated chromophore is present adjacent the lower end face of the electrode 6. Part of the beam 4 impinges upon the electrode 6, but the remainder of the beam 4 passes below the lower end face of the electrode 6. Although most of the beam passing the electrode 6 is not diffracted and forms a central spot on a screen 10, part of the beam 4 is diffracted as it passes the electrode 6, as exemplified by the diffracted beams 12 and 14.

Although simplified, FIG. 1 does illustrate several of the important advantages of the invention. It will be seen that the beam 4 passes through a thickness of the diffusion layer 8 which is equal to the thickness of the electrode 6. This is in contrast to most prior art spectroelectrochemical methods, in which the beam only passes through the diffusion layer over a path length approximately equal to the thickness of the layer (the thickness of the diffusion layer 8—its dimension perpendicular to the end face of the electrode 6—is greatly exaggerated in FIG. 1 for the sake of clarity). In addition, the major contribution to the intensity of the diffracted radiation comes from radiation passing very close (within a few micrometers) of the electrode surface; light passing at much greater distances from the electrode is not appreciably diffracted so that, to a reasonable approximation, the diffracted light has all passed through the region of interest close to the electrode. Not merely does this mean that only a very thin diffusion layer is needed, so that the method responds very rapidly to the generation of chromophores at the electrode, and thus it is practicable to use the method with modulation of the potential at the electrode, but, as will be explained in more detail below, the diffracted radiation contains spatial information about the distribution of the chromophore within the diffusion layer. Finally, it should be noted the diffracted radiation is present both above and below the main beam 4, but in practice it is much more convenient to observe the diffracted radiation above the undiffracted beam because this region is in shadow and thus substantially the only radiation present on this part of the screen will be the diffracted radiation.

A theoretical analysis of the intensity of the diffracted radiation observed on the screen 12 in FIG. 1 may be made as follows. To correlate the theoretical results obtained with actual experimental results, it is desirable to analyze absorbance, that is to say the ratio of the intensity observed without the chromophore present to that absorbed with the chromophore present, at a particular point on the screen 10 and at a particular time after initiation of electrolysis. As shown in FIG. 1, the diffracting object is a surface with finite thickness along the optical axis (i.e. the axis of the beam 4, designated Z in FIG. 2). Although in theory Maxwell's equations describe the diffraction of radiation by any object, the full mathematical treatment of diffraction by a surface having finite thickness along the optical axis is exceedingly complex. However, we have found that with electrode dimensions likely to be used in practice (typically of the order of 0.1 to 20 mm.) the observed intensities agree closely with those predicted by treating the electrode as a simple plane having an infinitely thin edge.

The case of diffraction by an infinitely thin edge is treated in the following publications.

A. M. Born and M. Wolfe, Principles of Optics, Third Edition, Pergamon Press, New York (1964);

M. Herzberger, Modern Geometrical Optics, Interscience, New York, (1958);

R. S. Longhurst, Geometrical and Physical Optics, Longmans, New York (1957); and D. Marcuse, Light Transmission Optics, Van Nostrand Reinhold, New York, (1972).

Figure 2:
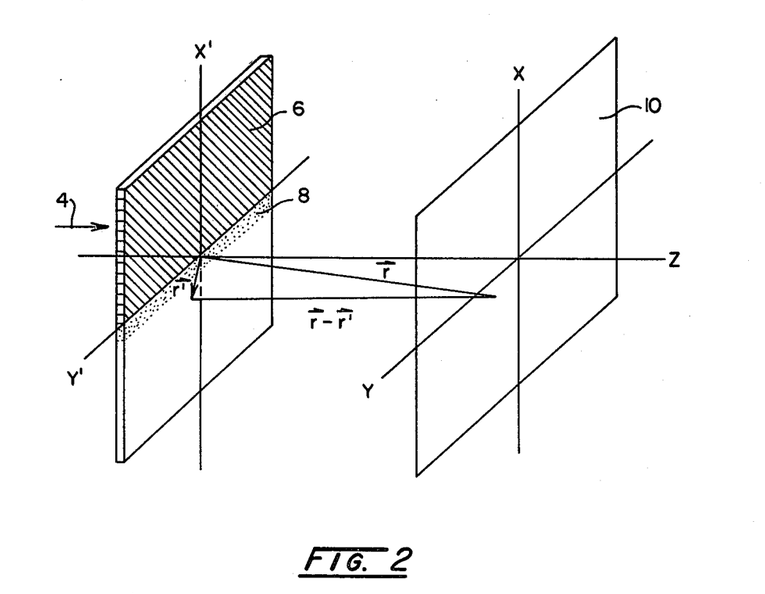
FIG. 2 shows the coordinate system used in the theoretical derivation of the intensity of the diffracted light produced on the screen shown in FIG. 1.

The Cartesian coordinate system used in the following mathematical analysis is shown in FIG. 2. As previously mentioned, the Z axis is along the optical axis of the beam 4. The Y axis lies in the plane of the screen 10 parallel to the lower edge of the electrode 6. The X axis is taken in the plane of the screen 10 perpendicular to the Y and Z axes. The origin of coordinates thus lies at the point where the optical axis of the beam 4 strikes the screen 10. Additional X' and Y' axes are shown parallel to the X and Y axes respectively but lying in the plane of the (hypothetical) infinitely thin electrode 6.

Using the coordinate system shown in FIG. 2, the diffracted intensity at a point (x, y, z) on the screen can be calculated by Kirchoff-Huygens diffraction theory; this theory is discussed in the Longhurst work cited above at page 193 and in the Marcuse work cited above at page 31. Kirchoff-Huygens diffraction theory essentially states that the amplitude of light at a point on the screen is the sum of all contributions from the original beam, as if each point in the beam at the electrode were a spherical radiator. Applying this theory to the point $\bar{r}$ having coordinates (x, y, z) gives the equation:

$$A(\bar{r}) = \frac{ik}{2\pi} \int_{-\infty}^{\infty} \int_{-\infty}^{\infty} \frac{\exp(-ik|\bar{r} - \bar{r}'|)}{|\bar{r} - \bar{r}'|} \psi(x',y')dx'dy' \quad (1)$$

where A ($\bar{r}$) is the amplitude at point $\bar{r}'=(x', y', 0)$ and denotes the coordinates of a point on the plane of the side of the thin electrode nearer the screen. k is the wave number of the incident light ($2\pi$ divided by the wave length $\lambda$), and $\psi(x', y')$ is the amplitude of the radiators in the plane of the trailing side of the electrode.

The integration is taken over the whole plane of the trailing side of the electrode. On the electrode itself, $\psi(x'y')$ is 0 so that, in FIG. 2, $\psi(x',y')=0$ for all x' greater than 0. On the remainder of the (x',y') plane, the amplitude is assumed to be determined by the aborbtivity of the diffusion layer contaning the electrogenerated chromophore in accordance with Beer's law. Thus, for x' less than 0, $\psi(x'y')$ is given by:

$$\psi(x',y')=I_o^{\frac{1}{2}}(x',y')10^{-\epsilon bC(x')/2} \quad (2)$$

where $I_o(X',y')$ is the intensity of the incident light (in this case a circular gaussian beam);

$\epsilon$ is the extinction coefficient of the chromophore at the frequency of the incident light;

b is the length of the electrode along the optic axis; and

C(x') is the concentration of the chromophore at the point (x', y'), which is in the present case is independent of y'.

In the case of at stable electrogenerated chromophore, C(x') may be calculated from the standard linear diffusion equations; in the case of unstable chromophores, methods are available for calculating the concentration of chromophores at particular distances from the electrode, these methods in effect adding to the equations for the stable chromophores a term representing the decay of the chromophore.

It should be noted that the above mathematical theory is not restricted to any particular form of the amplitude function $\psi(x', y')$ and thus this amplitude function may represent any two dimensional shape with arbitrary optical density. Accordingly, the theory may be used to treat the case of diffraction by slits or apertures or any other electrode configuration.

Equations (1) and (2) completely determine the intensity at the screen for diffraction from a thin electrode, neglecting only surface effects and diffractive effects associated purely with the finite thickness of the electrode (although in practice there are a few other errors caused by, inter alia, changes in refractive index of the solution as change in chemical composition occurs during generation of the chromophore—though in practice such changes are likely to be extremely small). The mathematical approximations made below are only for convenience in evaluating the integral in Equation (1) and may, if necessary, be discarded and the integral evaluated directly by numerical methods.

Depending upon the distance from the screen to the electrode, Equation (1) may be simplified by either of the two standard simplifying approximations, namely the Fresnel and Fraunhofer approximations. The Fresnel approximation is useful at small screen-electrode distances and small diffraction angles but although the resultant integral can be evaluated by standard numerical methods, it is more complex than the Fraunhofer approximation. The Fraunhofer approximation is useful at large screen-electrode distances and yields a simple expression for the amplitude of the diffracted light. Measurement of the diffracted light in the Fraunhofer region is preferred for practical reasons because in the Fraunhofer region the diffracted light has been scattered significantly away from the main beam and can thus be measured without interference from the main beam, whereas in the Fresnel region it is necessary to measure relatively small changes in the intensity of the main beam.

In the Fraunhofer region, where the modulus of $\bar{r}$ is very much greater than that of $\bar{r}'$, the distance $|\bar{r}-\bar{r}'|$ appearing in Equation (1) may be approximated:

$$|\bar{r} - \bar{r}'| \sim z + \frac{(x^2 + y^2)}{2z} - \frac{(xx' + yy')}{z} \quad (3)$$

in the exponential term and by z, the distance from the electrode to the screen in the denominator. A(r) then reduces to a conventional Fourier transform:

$$A(\bar{r}) = \frac{ik}{2\pi z} \exp\left(-ik\left(z + \frac{(x^2 + y^2)}{2z}\right)\right) \int_{-\infty}^{\infty} \int_{-\infty}^{\infty} \exp\left[i\left(\frac{kx}{z}\right)x' + i\left(\frac{ky}{z}\right)y'\right] \psi(x',y')dx'dy' \quad (4)$$

This expression for A($\bar{r}$) is valid for any arrangements of slits or apertures in the electrode, but may be further simplified in the case shown in FIG. 2 where the only variation in the diffraction pattern which is desired to measure is that along the coordinate x. In this case, the incident circular Gaussian beam having amplitude function $\psi(x', y')$ is separable into a product of functions of x' and y':

$$\psi(x',y')=\psi(x')\rho(y') \quad (5)$$

Accordingly, the result of the integration over y' and the other y-dependent factors in Equation (4) may be combined into a single function a(y) which is constant at a fixed value of y. A($\bar{r}$) is then given by:

$$A(\bar{r}) = ika(y)(2\pi z)^{-1}\exp[-ikz - \quad (6)$$

-continued $$ikx^2(2z)^{-1}] \int_{-\infty}^{\infty} \phi(x')\exp(ikxx'z^{-1})dx'$$

where $\phi(x')$ is given by:

$$\phi(x') = [i_o(x')]^{\frac{1}{2}} 10^{-\epsilon b C(x')/2} \quad (7)$$

where $i_o(x')$ is the intensity of the incident beam as a function of $x'$ and $\phi(x')$ is the $x'$-dependent factor when the function $\psi(x', y')$ in Equation (2) is separated into the product of functions of $x'$ and $y'$.

Figure 3:
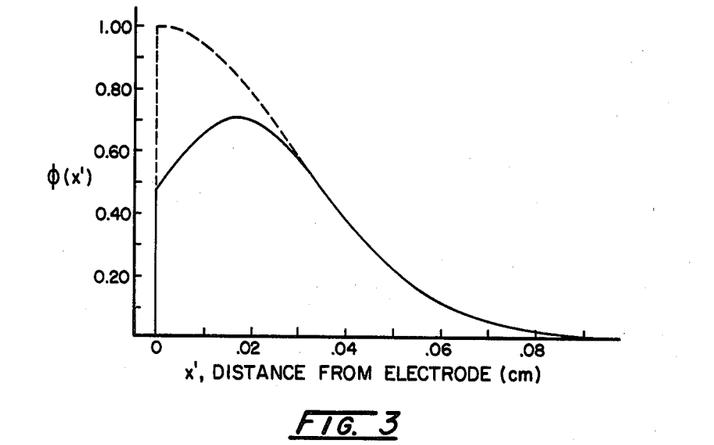
FIG. 3 shows the amplitude function at the electrode, the broken line representing a Gaussian laser beam truncated at its center by an opaque electrode and the solid line the same curve with an electrogenerated chromophore present.

The function $\phi(x')$ is shown in FIG. 3 for the apparatus shown in FIG. 1 both with and without the chromophore present. The broken line shows the function without chromophore present, while the solid line shows the same function after generation of a stable chromophore which diffuses linearly away from the electrode surface.

When the amplitude function $A(\bar{r})$ in Equation (6) is squared to convert it to an intensity function, the term preceding the integral becomes a constant independent of the presence of chromophore or the x-coordinate on the screen. It is then necessary to consider only the integral in Equation (6), which is simply the Fourier transform of the amplitude function $\phi(x')$. Once $\phi(x')$ has been calculated from the properties of the chromophore, the integral can be evaluated by a number of standard known numerical techniques, including the fast Fourier transform algorithms often used in x-ray crystallography. Thus, if the concentration function $C(x')$ and the intensity profile of the incident laser beam are known, the intensity $|A(\bar{r})|^2$ can be calculated as a function of the screen coordinate x for any given values of z and y. Furthermore, if it is desired to calculate only relative intensities as a function of the screen coordinate x (as will usually be the case, since experimentally it is very difficult to measure absolute intensities of the diffracted beam) the pre-exponential constant in Equation (6) need not be calculated.

It should be noted that the Fraunhofer diffraction patterns obtained using the apparatus shown in FIG. 1 are in accordance with the general rule that the Fraunhofer diffraction pattern is the Fourier transform of the amplitude function which generates it. As shown below, this rule is important when considering the diminution of the beam caused by the chromophore at various diffraction angles.

Equation (6) also provides a theoretical basis for determining the shape of any concentration profile from the Fraunhofer diffraction pattern produced thereby. The inverse transformation necessary to produce the concentration profile from the diffraction pattern is analogous to determining crystal structures by X-ray diffraction, except of course that in the instant method radiation having a longer wave length than x-rays (and usually in the visible or ultraviolet range) is used to determine profiles having features of the dimensions of the wave length of the radiation employed. Also, in the instant method, only a one-dimensional profile is sought, not a three-dimensional structure. Applying an inverse Fourier transformation to both sides of Equation (6) gives the following equation:

$$\phi(x') = [ia(y)]^{-1}\exp(ikz + ikx^2/2z) \int_{-\infty}^{\infty} \exp(-ikx'x/z)A(\bar{r})dx \quad (8)$$

thus, if the amplitude $A(\bar{r})$ at the screen is known, $\phi(x')$ can be determined and the concentration against distance $x'$ profile deduced.

As in x-ray crystallography, one major problem in such inverse transformation is that, since only the intensity of the diffracted light can be measured at the screen, all information regarding the phase of the diffracted light is lost unless specialized experiments using interferometry are performed. In the apparatus shown in FIG. 1 in which the radiation passes parallel to only a single edge of an electrode, the diffracted light can have any phase relative to the main beam, and this makes the phase problem especially severe, in a manner comparable to that experienced when using non-centrosymmetric crystals in x-ray crystallography. To reduce the phase problem, it is preferred to use the variant of the instant method in which either light is diffracted from two parallel surfaces of the electrode, these parallel surfaces either being in the form of parallel walls defining a slit or (more conveniently) in the form of parallel surfaces on either side of a thin electrode or in which the electrode has a circular aperture therethrough. Since in such an arrangement the amplitude function of the incident light is symmetrical about a plane, the phase of the diffracted light in such an arrangement can only be either in phase or 180° out of phase with the main beam, in a manner similar to that experienced using a centrosymmetric crystal in x-ray crystallography.

Figure 4:
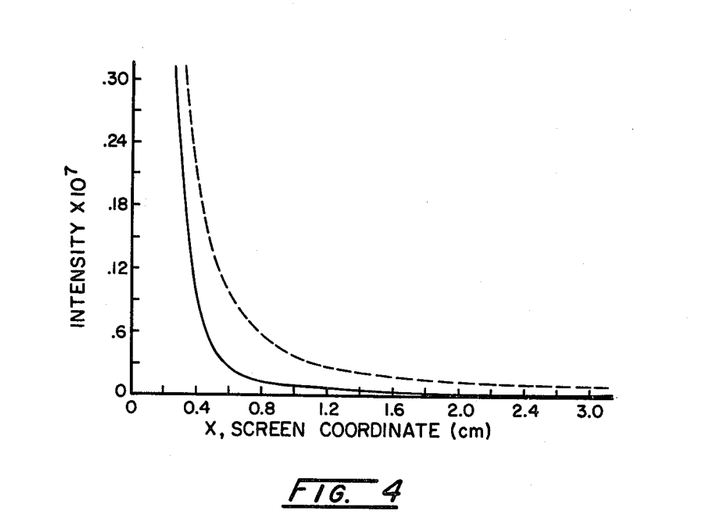
FIG. 4 shows the diffraction patterns for the amplitude functions of FIG. 3, calculated by Fourier transform and conversion from amplitude to intensity.
Figure 5:
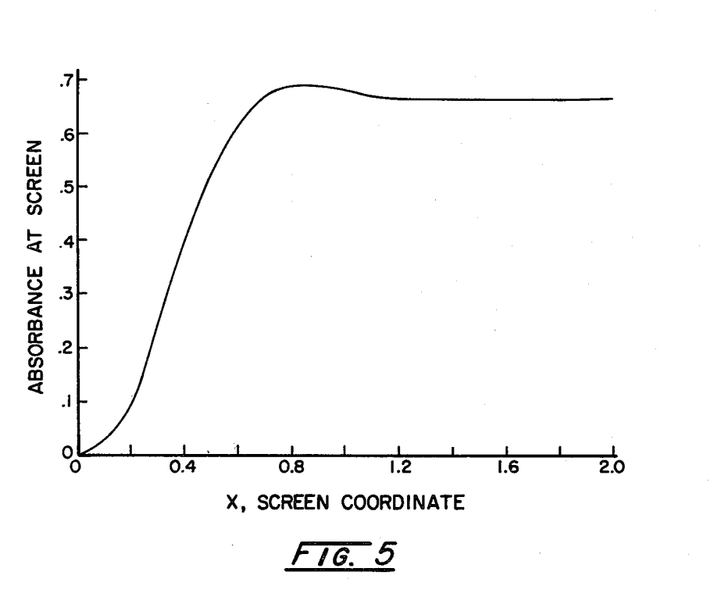
FIG. 5 shows the absorbance measured at the screen shown in FIGS. 1 and 2 as a function of the screen coordinate, calculated from the solid curve shown in FIG. 4.

FIG. 4 shows the square of the moduli of the Fourier transforms of the amplitude functions shown in FIG. 3. Again, the broken line represents the curve obtained from a bare edge without the presence of chromophore, while the continuous line shows the curve obtained when electrogenerated chromophore is present. Since the pattern is symmetrical about $x=0$, the curves are shown for positive values of the coordinate x; intensity rather than amplitude is plotted to permit direct comparison with experimental values. FIG. 4 shows that the diffraction pattern for an edge does not display the classic oscillatory Fresnel pattern but instead shows a smooth curve analogous to a $x^{-2}$ curve. The actual parameters used in calculating the solid curve in FIG. 4 are those used experimentally in the apparatus described below with reference to FIG. 7. Comparison of the two curves in FIG. 4 shows that the intensities at the larger angles are attenuated more, as may be more readily seen from FIG. 5, which shows the absorbance produced by the chromophore, as calculated from the curves in FIG. 4. This is to be expected, since the larger diffraction angles represent the higher Fourier frequencies required to synthesize the original amplitude distribution at the electrode. Accordingly, the higher angles of diffraction represent the very high frequency required to describe the sharpness of the original edge. As the chromophore is electrogenerated, the edge in effect becomes less sharply defined and thus the higher Fourier frequencies become less important. To put it another way, the optical density distribution near the electrode in the absence of chromophore is composed of higher Fourier frequencies than the more diffuse distribution obtained when chromophore is present.

Figure 6:
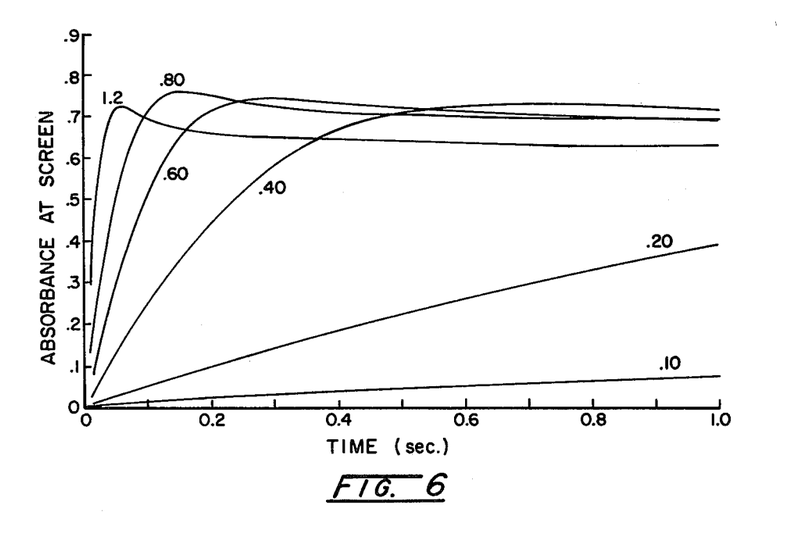
FIG. 6 shows a series of theoretical absorbance against time profiles for various diffraction angles.

As electrolysis progresses, the shape of the curves depicted in FIG. 3 changes as chromophore diffuses away from the electrode surface at which it is generated. By evaluating the Fourier transform in Equation (6) for a series of amplitude functions $\phi(X')$ corresponding to concentration profiles at different times after the start of electrolysis, a plot of the intensity of the diffracted radiation at a given angle can be obtained as a function of time after the beginning of electrolysis. FIG. 6 shows a series of such intensity against time curves for different diffraction angles (the Figures adjacent each curve represent the diffraction angle in degrees) assuming simple linear diffusion; the absorbance plotted is the log of the ratio of intensity prior to electrolysis to that after electrolysis begins. FIG. 6 illustrates several important features of the invention. Firstly, the response time is very short, particularly at higher diffraction angles, with 0.55 absorbance units being reached in 25 msec at a diffraction angle of 1.2°. This absorbance is 76 times that expected under the same conditions for an optically transparent electrode of conventional design. Secondly, after "long" electrolysis times (anything over about one second for diffraction angles of 0.40° and above) the absorbance reaches a constant value of 0.65 absorbance units regardless of the diffraction angle. This constant value of 0.65 is the value calculated from Beer's law using the electrode dimension along the optical axis as the path length and a chromophore concentration equal to the bulk precursor concentration. This limiting value is reached when all the precursor in the region near the electrode has been converted to chromophore so that the chromophore concentration in the layer from which the diffracted light comes has the same concentration as the original bulk precursor. This is optically equivalent to attenuating the entire input beam, and thus all diffracted light is attenuated equally at long electrolysis times. It should be noted that the higher angles reach this limiting value more quickly again because the higher diffraction angles correspond to higher spatial frequencies derived from regions close to the electrode. Although there is not a 1-to-1 correspondence between diffraction angle and distance from the electrode, the light diffracted at higher angles does have a greater contribution from events close to the electrode surface.

Thirdly, as has been mentioned above, the diffracted light contains spatial information about the concentration of the chromophore at various distances from the electrode surface since the absorbance against time curve is highly dependent on diffraction angle. As the shape of the diffusion layer of chromophore changes, so does the distribution of diffracted light. It is theoretically possible to perform an inverse transformation on the diffraction pattern to obtain the distribution of chromophore as a function of distance from the electrode.

Figure 7:
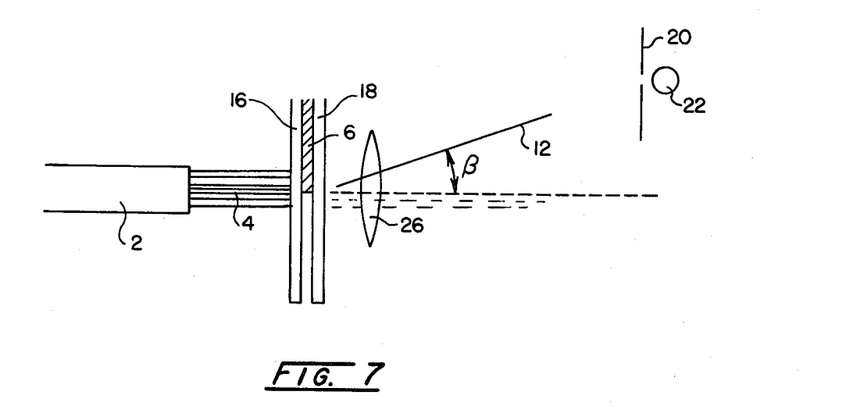
FIG. 7 shows schematically a practical form of apparatus of the invention.

A practical apparatus of the invention is shown schematically in FIG. 7. As in the apparatus shown in FIG. 1, a laser 2 projects a beam 4 of visible radiation onto the lower edge of an electrode 6 which partially occludes the beam 4. In this apparatus, the laser 2 is a 5 milliwatt helium-neon laser operating at a wave length of 632.8 nm. The electrode 6 was a platinum electrode having a thickness of 0.5 mm. along the optical axis, and the exposed lower surface was polished to a mirror finish with alumina. The platinum electrode was sandwiched between glass shields 16 and 18 which ensurerd linear diffusion and defined the boundaries of the electrochemical cell. To ensure that the laser beam 4 was accurately parallel to the lower surface of the electrode 6, the laser beam was directed onto the electrode by a beam steering device and the electrode rotated relative to the beam. The electrode was first positioned so that part of the beam was reflected off its lower surface, and the electrode was then rotated until the reflected and non-reflected beams coincided.

Adjacent the trailing glass shield 18 is positioned a converging lens 26. The screen 10 in the apparatus shown in FIG. 1 is replaced by a light detector comprising a photomultiplier tube 22 positioned behind a moveable screen 20 having a circular aperture of 0.8 mm. diameter therethrough. The focal length of the lens 26 was 36.5 centimeter and the screen 20 was positioned in the focal plane of the lens.

The solution to be analyzed is introduced into the cell formed by the glass shields 16 and 18 from below and is in fluid contact with a cell containing the reference and auxiliary electrodes. The potential applied to the electrode 6 is determined by a conventional commercially-available potentiostat under the control of a computer. The output from the photomultiplier 22 was also fed to the computer so that correlations could be made between the potential applied to the electrode and the signal received by the photomultiplier. The photomultiplier was moveable by means of a micrometer stage and the entire apparatus was mounted on a vibration-isolated optical table. It should be noted that the photomultiplier tube is positioned in the shadow of the electrode; since the diffracted intensity is symmetrical about the point where the main beam 4 passes through the focal plane of the lens, it is more convenient to position the photomultiplier within the shadow of the electrode to minimize interference from stray light caused by refraction or other non-diffractive scattering.

The lens 26 imposes the Fraunhofer condition necessary to validate the Fourier transform. Without such a lens, it is necessary to position the photomultiplier tube 22 several meters from the electrode. The use of such long path lengths is extremely inconvenient, especially since for practical reasons it is necessary to mount the photomultiplier tube and the electrode upon the same vibration-isolated surface in order to prevent relative movement between the two which might give rise to false readings. A detector positioned in the focal plane of the lens samples light which was parallel when it entered the lens, and this requirement for parallel light input into the lens automatically validates the Fraunhofer approximation, since the screen is effectively positioned at infinity. Each point on the focal plane of the lens receives light of a particular Fourier frequency X, given by:

$$X = Zm\lambda/2L$$

where

Z = the focal length of the lens;

m = the component of the numerical Fourier transform; and

L = physical width of the input to the transform algorithm.

The mathematical theory developed above assumed that the entire diffraction process occurred within a medium of constant refractive index. In practice, of course, the diffraction takes place in a solution layer the refractive index of which is not equal to that of the air in which the diffraction pattern is measured. For example, in some of the experiments described below, the diffraction takes place in acetonitrile, the refractive index of which is 1.34, but the diffraction pattern is observed in air having a refractive index of 1.00. However, a correction for the refraction occurring at the phase boundary is not necessary because the change in direction of the diffracted light at the phase boundary is automatically compensated by the diffraction process. To show this, suppose that the entire experiment were performed in a solvent of refractive index $n_s$. The wave length $\lambda_s$ in this solvent is given by:

$$\lambda_s = \lambda_{air}/n_s. \quad (9)$$

In this solvent, equation (9) becomes $$\sin\alpha = X_s/Z_s = m\lambda_a/Zn_sL, \quad (10)$$

where $\alpha$ is the angle of diffraction within the solvent when the resultant diffracted light passes into air, the observed angle of diffraction ($\beta$) will be larger than $\alpha$ according to Snell's law:

$$\sin\alpha = \sin\beta/n_s \quad (11)$$

From equations (10) and (11):

$$\sin\beta = \frac{X_a}{Z_a} = \frac{m\lambda_a}{2L} \quad (12)$$

It will be seen that equation (12) is identical to equation (9) except that $\beta$ is the apparent diffraction angle measured in air.

EXAMPLE 1

The apparatus shown in FIG. 7 was used to analyze the 1-electron oxidation of trianisylamine (TAA) at 0.8 volts against a standard calomel electrode in acetonitrile. According to N. Winograd and T. Kuwana, Analytical Chemistry, 43, 252 (1971) the diffusion coefficient of the cation in 0.1 M tetraethylammonium perchlorate is $1.4 \times 10^{-5}$ cm.$^2$ sec$^{-1}$ and the molar absorptivity at 623.8 nm is known to be 10,750 M$^{-1}$ cm.$^{-1}$.

Figure 8:
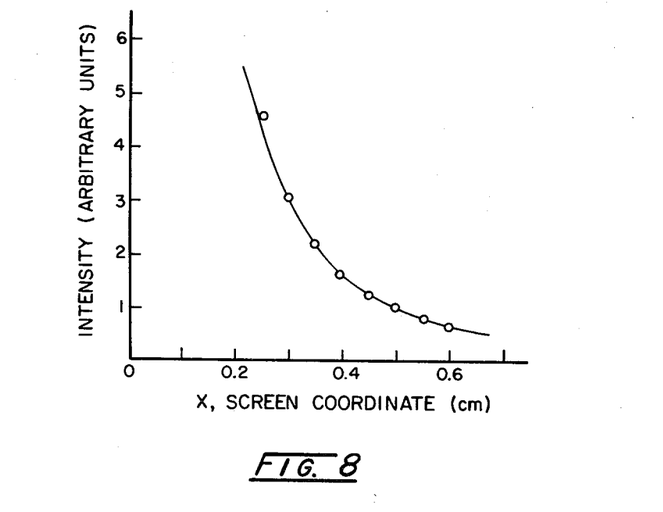
FIG. 8 shows a comparison of the observed and theoretical values of intensity against screen coordinate for the apparatus shown in FIG. 7 before solution is placed adjacent the electrode.

Experimental observations of the intensity of the diffracted light obtained from the apparatus shown in FIG. 7 in the absence of chromophore or solution in the cell are shown in FIG. 8 superimposed upon the theoretical curve predicted for diffraction by a thin edge in the absence of chromophore. Since the intensity scale is arbitrary, no absolute measurements of the intensity of the diffracted light having been obtained, the theoretical curve was scaled to obtain the best fit with the experimental observations. However, the screen coordinate scale is absolute, and thus the results shown in FIG. 8 indicate that the change in intensity of diffracted light with angle is as predicted by theory. Also, these results indicate that a 0.5 mm thick edge diffracts light in substantially the same manner as an infinitely-thin edge for these angles.

Figure 9:
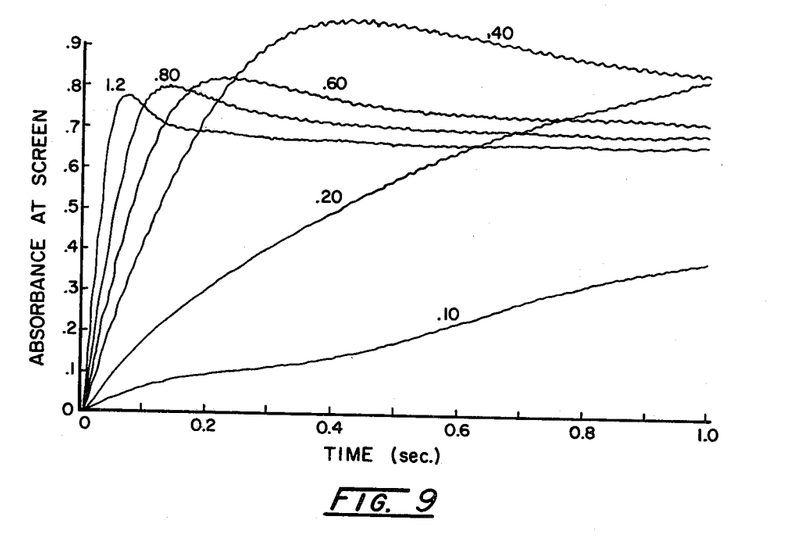
FIG. 9 shows various experimental absorbance versus time curves at differing diffraction angles for the oxidation of trianisylamine in acetonitrile observed using the apparatus shown in FIG. 7.

To check the agreement between theory and practice regarding the behavior of the diffraction pattern as the chromophore is generated at the electrode, it is experimentally more convenient to observe intensity changes at a particular screen coordinate as a function of time after the beginning of electrolysis. Experimental absorbance against electrolysis time curves at various angles of diffraction are shown in FIG. 9. The absorbance is measured as the log of the ratio of intensity before electrolysis began to the ratio at particular times after electrolysis commenced, and the figures on the various curves show the diffraction angles in degrees. Comparison of FIGS. 6 and 9 shows good agreement between the theoretical curves in FIG. 6 and the experimental observations in FIG. 9, thus again confirming that a 0.5 mm thick electrode does diffract light in substantially the same manner as the infinitely-thin electrode assumed in the theoretical calculations. Comparing FIGS. 6 and 9, it will be seen that the greatest deviations between theory and practice occur at very small diffraction angles. These deviations are believed to be due to the difficulty of measuring such small angles with the requisite accuracy. Moreover, small errors in alignment and positioning of the electrode relative to the beam affect the results at small angles more than those at larger ones.

Another potential source of error is the phase shift of the light caused by changes in the refractive index as the substrate is oxidized. However, the resultant error appears to be small, as would be expected considering that methods used to measure refractive index changes in the diffusion layer require concentrations of the order of 0.1 M, about 100 times larger than those used in the experiment.

The experimental results shown in FIG. 9 confirm the theoretical predictions that the instant method gives a very rapid response time, especially at larger diffraction angles. Note that at 1.2°, 0.8 absorbance units are attained after only 70 msec. At even higher angles, a faster response is possible, but a more powerful laser is needed to provide sufficient diffracted light at higher angles for proper observations. Even with a more powerful laser, it will usually be convenient to observe the diffraction at angles of not more than about 10° since at larger angles the intensity of the diffracted light is small. The experimental absorbance value at 70 msec. and 1.2° diffraction angle is 120 times that obtained for an optically transparent electrode under similar conditions, thus giving an improvement in sensitivity of over two orders of magnitude. Moreover, as predicted by theory, the experimental absorbance values tend to a constant value at long electrolysis times, this constant value being independent of the angle of diffraction, this constant absorbance corresponding to a substantially homogenous distribution of chromophore in the region adjacent the electrode. The variation in diffracted intensity with angle and time at shorter electrolysis times confirms that the diffraction pattern is sensitive to the spatial distribution of the chromophore, each distinct diffraction pattern being derived for a different concentration distribution of the chromophore in the layer of solution adjacent the electrode.

EXAMPLE 2

The apparatus shown in FIG. 7, with the 13 millimeter thick electrode, was used to monitor the electrochemical oxidation of tri-(p-bromophenyl)amine to its cation radical which has $\epsilon = 15,400$ at 632.8 mm. The amine was dissolved at a concentration of $10^{-5}$ M in acetonitrile and the diffracted light was measured at an angle of 2.7°. The results are shown in FIG. 10, in which the absorbances are expressed relative to the intensity of the diffracted light prior to the commencement of electrolysis.

Figure 10:
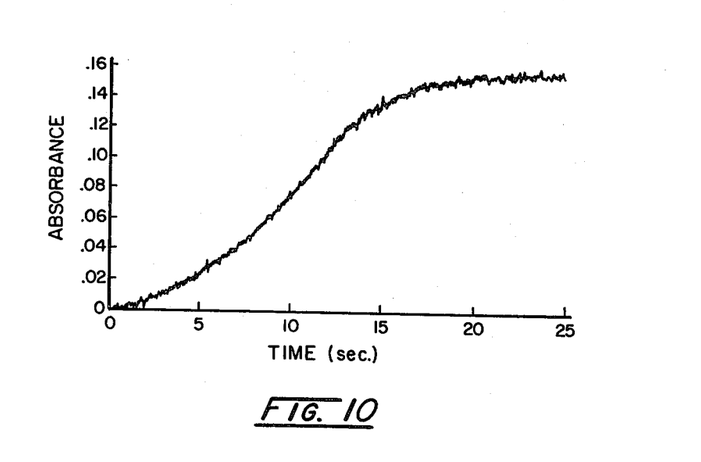
FIG. 10 shows an experimental absorbance versus time curve for the oxidation of tri(p-bromophenyl)amine in acetonitrile observed using the apparatus shown in FIG. 7.

It will be seen from FIG. 10 that substantially full absorbance was achieved after 25 msec. and that the absorbance reached was approximately 0.15, even at the low amine concentration employed. This absorbance figure is 1,750 times that achievable with a conventional optically-transparent electrode at the same amine concentration and electrolysis time.

EXAMPLE 3

The same electrochemical oxidation as in Example 2, namely the oxidation of tri(p-bromophenyl)amine to its cation radical, was conducted using the apparatus shown in FIG. 7 but using three different electrodes having thicknesses of 0.5, 0.27 and 0.14 mm. respectively. The diffracted light was measured at an angle of 0.54° after an electrolysis time of one second. The table below shows the experimental and predicted absorbance values; it will be seen that the agreement between the experimental and predicted absorbance values is good in all cases.

| CONCEN-TRATION (mM) | ELECTRODE LENGTH (cm) | ABSORBANCE EXPERIMENTAL | PREDICTED |
|---|---|---|---|
| 1.220 | .05 | .90 | .92 |
| 0.5976 | .027 | .24 | .24 |
| 2.158 | .027 | .86 | .88 |
| 2.378 | .027 | 1.06 | .97 |
| 3.329 | .027 | 1.40 | 1.36 |
| 5.698 | .014 | 1.20 | 1.20 |
| 6.035 | .014 | 1.32 | 1.28 |

EXAMPLE 4

A $10^{-4}$ M aqueous solution of 4,4'-dimethoxybenzidine was subjected to electrolysis using the apparatus shown in FIG. 7 but substituting an argon laser having a wave length of 515 nm. for the helium-neon laser shown in FIG. 7. 4,4'-Dimethoxybenzidine in aqueous solution undergoes a 2-electron oxidation to produce a doubly charged cation, two electrons and two protons. The neutral molecule does not absorb substantially at 515 nm, but the cation has a maximum absorption at 510 nm. and has $\epsilon = 22,700$ at 515 nm.

Figure 11A:
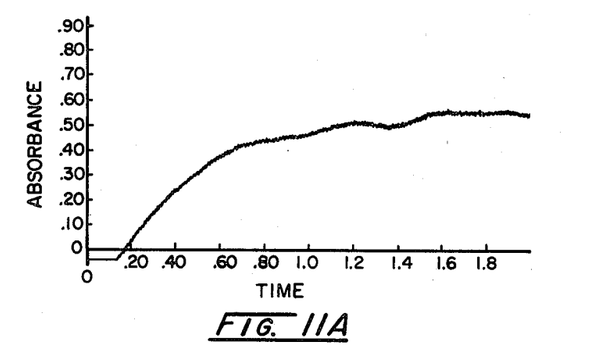
FIGS. 11A, 11B and 11C show various experimental absorbance versus time curves for the oxidation of aqueous 4,4'-dimethoxybenzidine observed using the apparatus shown in FIG. 7.
Figure 11B:
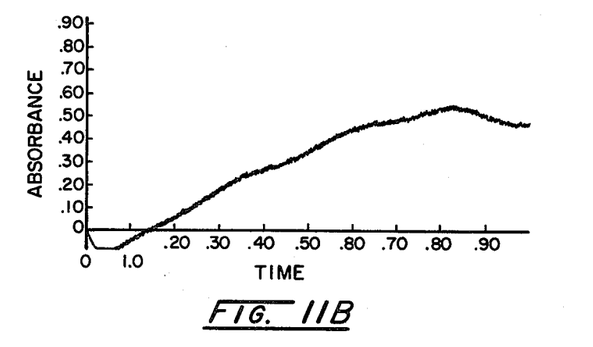
Figure 11C:
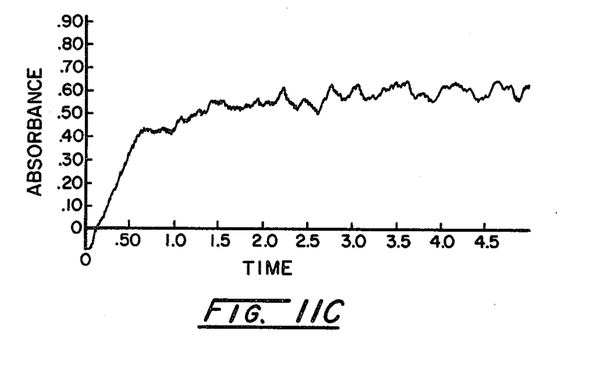

The diffracted light from the electrochemical cell was measured at an angle of 1.65° to the incident beam over a period of five seconds from the beginning of electrolysis. FIGS. 11B, 11A and 11C show respectively the measured intensity of the diffracted light over periods of one, two and five seconds. The absorbance curves shown in these figures agree well with theoretical predictions except for the first 0.2 seconds of electrolysis; from 0 to 0.15 seconds, the absorbance determined is negative, i.e. the intensity of the diffracted light *increases* after the beginning of the electrolysis. This abnormal behavior of the solution is believed to be due to a small amount of air oxidation of the dimethoxybenzidine; since the electrode was held at ground potential prior to the beginning of electrolysis, the dimethoxybenzidine in the layer of solution immediately adjacent the electrode was kept in the reduced form, whereas in the bulk solution some air oxidation could take place. Thus, at the beginning of electrolysis the presence of the air-oxidized dimethoxybenzidine in the bulk solution, with the layer of dimethoxybenzidine held in the reduced form adjacent the electrode, caused the diffraction pattern to resemble partially that caused by a slit rather than a simple edge, and such slits can give rise to negative absorbance values. Once a moderate amount of oxidation of the dimethoxybenzidine in the layer adjacent the electrodes has been accomplished, after about 0.25 seconds, this initial abnormality of the diffraction pattern is removed and the variation of the intensity of the diffracted light with time agrees closely with the theoretical predictions for diffraction by a single edge.

EXAMPLE 5

Figure 12:
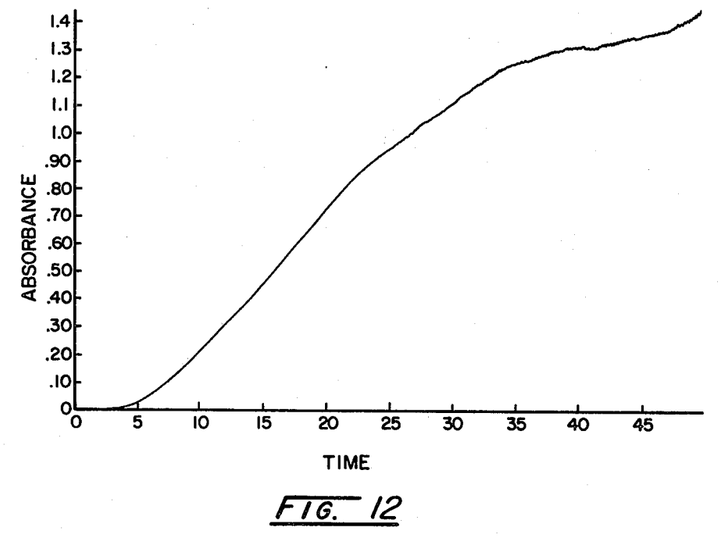
FIG. 12 shows an experimental absorbance versus time curve for the oxidation of tri(p-bromophenyl)amine in acetonitrile using the apparatus shown in FIG. 7 but with a change in the thickness of the electrode.

In the apparatus shown in FIG. 7, the 0.5 millimeter thick electrode was replaced by a 1.3 cm. thick electrode, the remaining parts of the apparatus remaining unchanged. A $10^{-4}$ M solution of tri(p-bromophenyl)amine in acetonitrile was placed in the cell and the photomultiplier 22 was arranged to collect light diffracted at an angle of 1.7° to the axis of the main beam. The absorbance obtained over the first 0.05 seconds is shown in FIG. 12, from which it will be seen that 1.4 absorbance units was achieved after only 50 msec. This absorbance is about 1,100 times that achievable with a conventional optically transparent electrode and the $10^{-4}$ M solution used. After "long" electrolysis times of the order of one second, the absorbance achieved gave good agreement with the theoretical Beer's low value, although with the very thick electrode some deviation was observed in the initial part of the electrolysis where the diffusion layer of electrogenerated chromophore was very thin relative to the electrode dimension along the optical axis.

The instant method has great potential for analysis of biological material. It may be applied to immunoassay in substitution for radioimmunoassay techniques by replacing the usual radio-labeled antigen with an antigen labeled with a suitable spectroelectrochemcial label such as the tri(p-bromophenyl)amine used in Example 2 above. The instant method is potentially so sensitive as to be competitive with radio-immunoassay and avoids the radioactive diposal problem inevitable with radio-immunoassay techniques. In addition, the bound antigen need not be separated from the unbound antigen, since bound antigens are either non-electroactive or have very low diffusion coefficients, making them substantially invisible to the method.

The instant method may also be applied to any biological material which is itself electrochemically active, for example, cytochromes and phenothiazine drugs. Such compounds may be monitored either in the original biological fluid or after chromatographic separation. Materials which are not themselves electrochemically active may be subjected to analysis by the instant method after formation of a derivative containing an electrochemically active group. For example, amino acids may be analyzed by forming their dinitrophenol derivitives, dinitrophenol having good absorbance at 442 mm. (the frequency of a helium-cadmium laser) and being electrochemically active.

We claim:

1. A method for the analysis of a layer of solution adjacent a surface of an electrode, said solution being capable of undergoing an electrochemical oxidation or reduction which alters its absorbance of electromagnetic radiation of at least one wavelength, said method comprising:

passing a beam of electromagnetic radiation at least part of which is of said wavelength across and substantially parallel to said surface;

measuring the radiation diffracted at an angle to said beam by means of radiation measuring means lying outside said beam;

altering the potential of said electrode, thereby causing at least part of said solution to undergo said electrochemical oxidation or reduction;

again passing said beam across and substantially parallel to said surface; and again measuring said radiation diffracted at an angle to said beam by means of radiation measuring means lying outside said beam.

2. A method according to claim 1 wherein said beam of radiation is monochromatic.

3. A method according to claim 2 wherein said beam of radiation is supplied by a laser.

4. A method according to claim 1 wherein said electromagnetic radiation is visible or untraviolet radiation.

5. A method according to claim 1 wherein the potential of said electrode is varied cyclically, and the variation of the intensity of said diffracted radiation with respect to time is determined.

6. A method according to claim 5 wherein said cyclic variation has a frequency of about 10 to about 200 Hz.

7. A method according to claim 6 wherein said cyclic variation has a frequency of at least about 50 Hz.

8. A method according to claim 5 wherein said measurement of at least part of said diffracted radiation is effected by a radiation detector and the output from said radiation detector is supplied to a lock-in amplifier.

9. A method according to claim 1 for measuring the diffusion of a chromophore produced by said electrochemical oxidation or reduction away from said electrode wherein the variation of the intensity of said diffracted radiation with respect to the time after said change of potential at said electrode is determined.

10. A method according to claim 1 wherein the intensity of said diffracted radiation is determined at a plurality of angles with respect to said beam of radiation.

11. A method according to claim 1 wherein said beam is passed simultaneously across two parallel surfaces of said electrode.

12. A method according to claim 11 wherein said parallel surfaces of said electrode comprise opposed faces of a laminar electrode.

13. A method according to claim 1 wherein said beam is passed through a aperture extending through said electrode.

14. A method according to claim 1 for immunoassay wherein said solution contains an antigen part of which is bound to an antibody and wherein said free and bound antigen differ in their electrochemical characteristics.

15. A method according to claim 1 wherein said solution contains a material which is not itself electrochemically active but at least part of which is in the form of a derivative containing an electrochemically active group.

16. A method according to claim 15 wherein said non-electrochemically active material comprises an amino acid and at least part of said amino acid is in the form of its dinitrophenol derivative.

17. A method according to claim 1 wherein said solution is a biological fluid.

18. Apparatus for analysis of a layer of solution adjacent a working electrode, said apparatus comprising;
a working electrode;
a counterelectrode;
means for applying a variable potential between said working electrode and said counterelectrode;
a beam generator for passing a beam of electromagnetic radiation across and substantially parallel to the surface of the working electrode;
a container for retaining liquid in contact with the surface of the working electrode; a converging lens disposed adjacent said working electrode on the opposed side thereof from said beam generator and
a radiation detector disposed substantially in the focal plane of said lens for detecting radiation diffracted at an angle to the beam, said radiation detector being disposed outside said beam.

19. Apparatus according to claim 18 wherein said beam generator comprises a laser.

20. Apparatus according to claim 18 wherein said radiation detector comprises a photomultiplier tube.

21. Apparatus according to claim 18 wherein said potential means includes means for cyclically varying the potential applied between said working and counter-electrodes, and wherein said apparatus further comprises a lock-in amplifier receiving the output from said radiation detector.

22. Apparatus according to claim 18 wherein said beam generator is arranged to pass said beam simultaneously across two parallel surfaces of said working electrode.

23. Apparatus according to claim 22 wherein said parallel surfaces of said working electrode comprise opposed faces of a laminar electrode.

24. Apparatus according to claim 18 wherein said working electrode has walls defining an aperture therethrough and said beam generator is arranged to pass said beam through the aperture passing through said working electrode.

25. Apparatus according to claim 18 wherein the dimension of said working electrode along the optic axis of said beam is about 0.1 to about 20 millimeter.

* * * * *